US00PP17300P3

(12) United States Plant Patent
NeSmith et al.

(10) Patent No.: US PP17,300 P3
(45) Date of Patent: Dec. 26, 2006

(54) RABBITEYE BLUEBERRY PLANT NAMED 'OCHLOCKONEE'

(50) Latin Name: *Vaccinium ashei*
Varietal Denomination: Ochlockonee

(75) Inventors: D. Scott NeSmith, Griffin, GA (US); Arlen D. Draper, Payson, AZ (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 481 days.

(21) Appl. No.: 10/646,660

(22) Filed: Aug. 22, 2003

(65) Prior Publication Data

US 2006/0095993 P1 May 4, 2006

(51) Int. Cl.
*A01H 5/00* (2006.01)

(52) U.S. Cl. ..... Plt./157
(58) Field of Classification Search ..... Plt./157
See application file for complete search history.

(56) References Cited

U.S. PATENT DOCUMENTS

PP10,675 P 11/1998 Lyrene ..... Plt./157

OTHER PUBLICATIONS

U.S. Appl. No. 10/255,211.

U.S. Appl. No. 10/909,650.

*Primary Examiner*—Kent Bell
*Assistant Examiner*—June Hwu
(74) *Attorney, Agent, or Firm*—,MacCord Mason PLLC

(57) ABSTRACT

*Vaccinium ashei* Reade 'Ochlockonee' is a Rabbiteye blueberry is distinguished by distinguished by its late bloom period, high and consistent productivity, large berry size, moderate chill requirement, late ripening, small berry scar, and high-quality fruit suitable for mechanical harvesting for the fresh market. The fruit of the plant is primarily used as fresh fruit for shipping, but is also suitable for customer-pick and processing markets.

1 Drawing Sheet

STATEMENT REGARDING FEDERALLY SPONSORED RESEARCH

The invention was made in part with Federal funds pursuant to the USDA Hatch Act, grant number 2001-3100-01635.

Genus and species of the plant claimed: *Vaccinium ashei* Reade.

Variety denomination: 'Ochlockonee'.

BACKGROUND OF THE INVENTION

1. Field of the Invention

The fruit of the plant is primarily used as fresh fruit for shipping. The fruit is also suitable for customer-pick and processing markets.

2. Description of Relevant Prior Art

The new and distinct variety of rabbiteye blueberry 'Ochlockonee', was selected in 1963 at the Coastal Plain Experiment Station in Tifton, Ga. from a cross of 'Tifblue' (non-patented)×'Menditoo' (non-patented) made in Beltsville, Md. and was tested as selection T-105. 'Tifblue' resulted from a cross of 'Ethel' (non-patented)×'Clara' (non-patented), and 'Menditoo' resulted from a cross of 'Myers' (non-patented)×'Black Giant' (non-patented). The selection was tested for several years and in the late 1980's, the selection was planted with 'Tifblue' at the University of Georgia's Blueberry Research Farm near Alapaha, Ga. Resulting data from several years indicate that 'Ochlockonee' is a high yielding late season variety, and should be widely adapted to areas conducive to rabbiteye blueberry production.

The male parent 'Menditoo' is only slightly improved from the wild species and was used primarily to improve berry size. It had very few other commercially desirable features. To the best knowledge of the inventor, it is not currently available for comparisons to be made. The new variety is most similar to 'Tifblue'.

'Ochlockonee' has been primarily compared with the late season rabbiteye standard 'Tifblue'. In Alapaha, Ga., productivity of 'Ochlockonee' exceeded that of 'Tifblue' in each of the past 5 years for plants that were established in 1986, and substantially exceeded that of 'Tifblue' ir. 3 of the 5 years. The 5 year average yield for 'Ochlockonee' in south Georgia was 67% greater than that of 'Tifblue', based on single bush, replicated plots. In addition to high yield, another important trait of 'Ochlockonee' as compared to 'Tifblue' is increased berry size, especially for first harvest berries. For each of the past 5 years the first harvest berries on 'Ochlockonee' plants established in 1986 were significantly bigger at the 5% probability level than berries of 'Tifblue'. The 5-year (1998–2002) average of annual yields was 17.0 lb. per plant for Ochlockonee compared to 10.1 lb. per plant for Tifblue, for plants grown in Alapaha, Ga. The 5 year average was 37% larger for first harvest 'Ochlockonee' berries, and was 25% larger for second harvest 'Ochlockonee' berries. These two properties alone make 'Ochlockonee' desirable as a highly productive, late season rabbiteye cultivar.

Other attributes such as berry scar, berry color, berry firmness, plant vigor, etc. for 'Ochlockonee' are comparable to 'Tifblue'. 'Ochlockonee' generally ripens a few days later than 'Tifblue', and bloom dates are similar which is favorable for escaping spring freeze damage in the south Georgia area. The estimated chill requirement of 'Ochlockonee' is 600 to 650 h, which is similar to or slightly higher than that of 'Tifblue'.

As for adaptation to other areas, young plants of 'Ochlockonee' planted in 2000 at Griffin, Ga. equaled 'Tifblue' in most attributes in 2002, except for crop load, which was greater for 'Ochlockonee', and ripening date, which was later for 'Ochlockonee'. In Stone County, Miss., 2 year old plant of 'Ochlockonee' and 'Tifblue' evaluated in 2002 were equal in plant vigor. The bush of the new cultivar is very "durable", since a planting of 'Ochlockonee' at Alapaha, Ga. that is more than 25 years old is still quite vigorous and productive.

The bush type of 'Ochlockonee' is vigorous and upright, with a fairly narrow crown. Plants have an abundant production of fruiting wood each year, with only moderate cane growth. Some stem disease lesions (*Gloeosporium minus* and/or *Septoria albopunctata*) have been observed on an older planting of 'Ochlockonee' in south Georgia, but several years of observations have indicated this has caused no serious production problems.

As with most rabbiteye blueberry cultivars, it is recommended that 'Ochlockonee' be planted with another rabbiteye cultivar with a similar bloom time for cross pollination. In south Georgia, the cultivars 'Brightwell' and 'Powderblue' would be suitable pollinizers for 'Ochlockonee'.

The new variety has been asexually propagated on many occasions since 1963 by softwood cuttings at Griffin, Ga. It roots readily from softwood cuttings and in all cases the clones propagated from cuttings have maintained the vegetative and fruit characteristics of the original selection.

SUMMARY OF THE INVENTION

Description and specifications of a new and distinct rabbiteye blueberry variety which originated from seed produced by a hand-pollinated cross of 'Tifblue'× 'Menditoo' is provided. The new 'Ochlockonee' variety can be distinguished by its late bloom period, high and consistent productivity, large berry size, moderate chill requirement, late ripening, small berry scar, and high-quality fruit suitable for mechanical harvesting for the fresh market.

DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a Rabbiteye Blueberry Plant Named 'Ochlockonee' (T-105).

BOTANICAL DESCRIPTION OF THE PLANT

The following is a detailed description of the botanical and pomological characteristics of the subject blueberry clone. Where dimensions, sizes, colors, and other characteristics are given, it is to be understood that such characteristics are approximations and averages set forth as accurately as practicable. Color data are presented in Royal Horticultural Society Colour Chart designations. The descriptions reported herein are largely from 14 year-old specimen plants grown in Alapaha, Ga. without supplemental irrigation and from 4 year-old plants grown in Griffin, Ga. with irrigation.

Plant:

*Size.*—Medium to large: plants were 2.0 to 2.5 m tall with an average canopy width of 1.5 m after 10 years without pruning. Some plants that are more than 20 years old are 3.0 to 3.5 m tall with a canopy width greater than 2.0 m.

*Growth habit.*—Plants are strongly upright, with only slight spreading. Crowns are narrow, with 6 to 8 major trunks.

*Growth.*—Medium to high vigor. Plants have abundant production of fruiting wood each year, with only moderate cane growth.

*Productivity.*—Very high; good consistency from year to year.

*Cold hardiness.*—Similar to other rabbiteye blueberry cultivars such as 'Tifblue' and 'Brightwell'.

*Chilling requirement.*—Plants require 600 to 650 hours of temperatures at or below 7 C. to induce normal leafing and flowering during the spring.

*Leafing.*—Plants readily break numerous leaf buds simultaneously with anthesis.

*Canes.*—Mostly erect, with only moderate branching. Main cane base diameter (15 year old plant) 50 mm, color Greyed-Green (198C); first major branch diameter 30–35 mm, color Greyed-Green (198C); 2 year old cane diameter 12–18 mm, color Greyed-Orange (164D), some flaking of bark; current season wood diameter 3–6 mm, color Green (138B).

*Fruiting wood.*—Numerous twigs 15–30 cm in length, with internode lengths of 15–20 mm common.

*Disease resistance.*—Somewhat tolerant of various defoliating leaf diseases; good tolerance to stem canker.

Foliage:

*Leaf color.*—Healthy mature leaves: top side of leaf Green (139A), under side of leaf Green (137C).

*Leaf arrangement.*—Alternate, simple.

*Leaf shape.*—Elliptic.

*Leaf margins.*—Crenate.

*Leaf venation.*—Mostly arcuate, with some netting.

*Leaf apices.*—Broadly acuminate.

*Leaf bases.*—Cuneate to acute.

*Leaf dimensions.*—Length 50 to 70 mm; width 25 to 35 mm.

*Leaf surface texture.*—Very waxy, smooth.

*Petioles size.*—Small, 3–4 mm long.

*Petioles color.*—Yellow-Green, 145B.

Leaves glabrous, except for occasional stalked glands along leaf margins.

Flowers:

*Color.*—White (155D) when fully opened, significant Red (55B) color on corollas just prior to bloom opening.

*Date of 50% antehesis.*—March 26 (5 year average).

*Flower shape.*—Urecolate.

*Flower bud number.*—High.

*Flower per cluster.*—5 to 8.

*Corolla aperture width.*—2.5 to 3.0 mm.

*Corolla width.*—5.8 to 6.3 mm.

*Fragrance.*—None.

*Peduncle.*—12.0 to 15.0 mm in length; Green 138B in color.

*Pedicle.*—5.0 to 6.0 mm in length; Green 138B in color.

*Calyx, with sepals.*—5.0 mm in diameter; Green 137D in color.

*Stamens.*—Number, 10 per flower; length, 7.0 to 8.0 mm; filament color, Green 142D.

*Anthers.*—Length, 4.0 to 4.5 mm; color, Greyed-Orange 171B.

*Style.*—Length, 9.0 to 10.0 mm; color, Yellow-Green 145B in color.

*Pistil.*—Length, 12.0 to 13.0 mm.

*Ovary.*—Color, Green 137D.

*Pollen.*—Yellow, 11C.

The cultivar has a small degree of self-compatibility.

Fruit:

*Date of 50% maturity.*—June 28 (5 year average).

*Fruit development period.*—94 days.

*Berry skin color.*—Blue 97C, with wax, Black 202A, wax removed.

*Berry flesh color.*—Green-White 157D.

*Berry size.*—Medium. First harvest average 1.40 g/berry, late season average 1.1 g/berry. Berries are 14 to 15 mm tall and 15 to 16 mm in diameter.

*Berry production.*—17 lb per plant based on 5-year (1998–2002) average of plants grown in Alapaha, Ga.

*Berry shape.*—Very rounded, nearly spherical.

*Fruit stem scar.*—Small, very dry, no tearing.

*Berry firmness.*—Good to excellent. Firmer than the cultivar 'Baldwin', similar to 'Tifblue'.

*Berry flavor and texture.*—Flavor sweet with mild to moderate acid level. Skins and seeds normal for rabbiteye cultivars.

*Storage quality.*—Good.

*Suitability for mechanical harvesting.*—Good.

*Uses.*—Can be used as fresh fruit for shipping, for customer-pick and processing markets.

*Seed dry weight.*—76.8 mg per 100 seed.

*Seed length.*—1.5 to 2.0 mm.

*Seed color.*—Greyed-Orange 166D.

What is claimed is:

1. A new and distinct variety of rabbiteye blueberry plant, substantially as illustrated and described, characterized by its late fruiting, high productivity and large berry size.

* * * * *

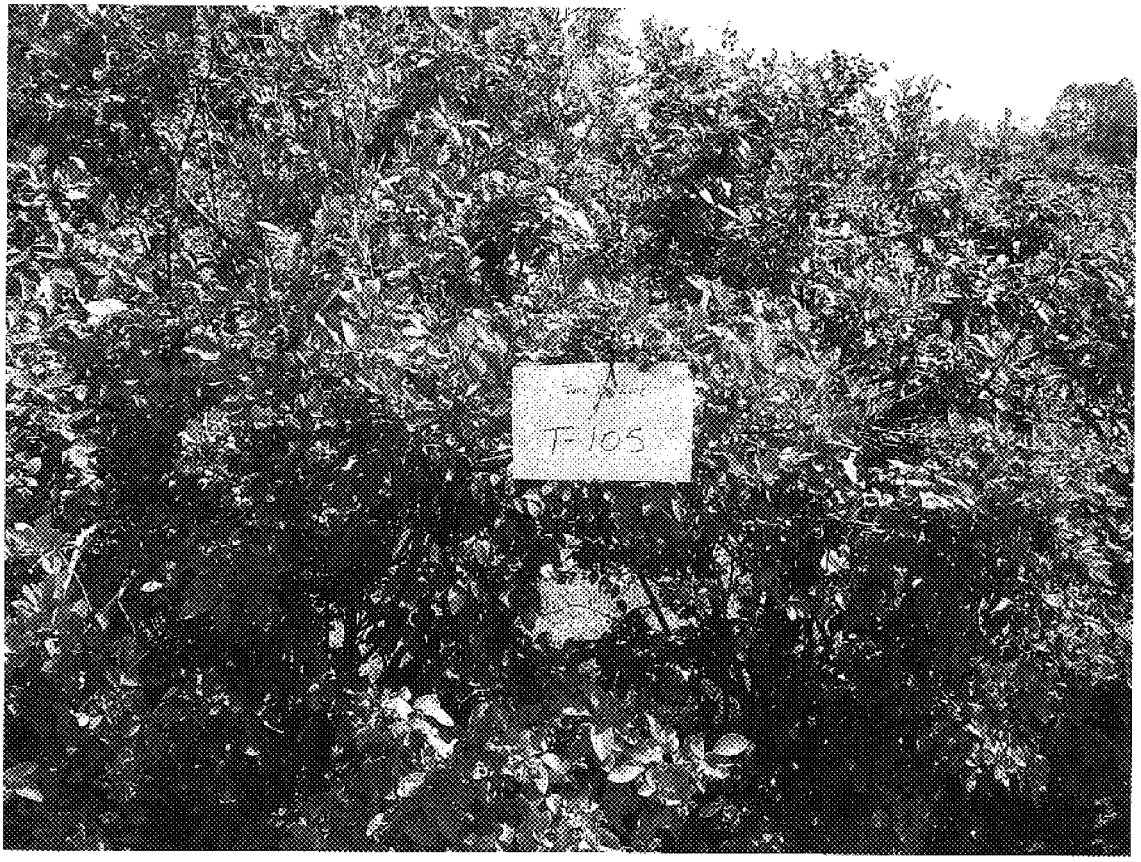
TF 105